(12) United States Patent
Turbett

(10) Patent No.: US 11,207,434 B2
(45) Date of Patent: Dec. 28, 2021

(54) METHOD AND APPARATUS FOR LOADING A FLOOR LOADING STERILIZER

(71) Applicant: Turbett Surgical, Inc., Rochester, NY (US)

(72) Inventor: Robert E. Turbett, Penfield, NY (US)

(73) Assignee: Turbett Surgical, Inc., Rochester, NY (US)

( * ) Notice: Subject to any disclaimer, the term of this patent is extended or adjusted under 35 U.S.C. 154(b) by 222 days.

(21) Appl. No.: 16/073,416

(22) PCT Filed: Jan. 27, 2017

(86) PCT No.: PCT/US2017/015303
§ 371 (c)(1),
(2) Date: Jul. 27, 2018

(87) PCT Pub. No.: WO2017/132488
PCT Pub. Date: Aug. 3, 2017

(65) Prior Publication Data
US 2019/0046672 A1 Feb. 14, 2019

Related U.S. Application Data

(60) Provisional application No. 62/288,864, filed on Jan. 29, 2016.

(51) Int. Cl.
| | | |
|---|---|---|
| *A61L 2/07* | (2006.01) | |
| *A61B 50/13* | (2016.01) | |
| *A61B 50/18* | (2016.01) | |
| *A61B 50/10* | (2016.01) | |
| *A61L 2/28* | (2006.01) | |

(52) U.S. Cl.
CPC ............... *A61L 2/07* (2013.01); *A61B 50/13* (2016.02); *A61B 50/18* (2016.02);
(Continued)

(58) Field of Classification Search
CPC ........ A61L 2/07; A61L 2/28; A61L 2202/121; A61L 2202/122; A61L 2202/14;
(Continued)

(56) References Cited

U.S. PATENT DOCUMENTS

| 3,994,684 A | 11/1976 | Tomasulo |
|---|---|---|
| 9,334,684 B2 | 5/2016 | Nam |

(Continued)

FOREIGN PATENT DOCUMENTS

| EP | 2404620 A1 | 1/2012 |
|---|---|---|
| WO | 2010/027527 A1 | 3/2010 |
| WO | 2010/060111 A1 | 5/2010 |

OTHER PUBLICATIONS

International Search Report and Written Opinion for corresponding International Application No. PCT/US2017/015303 dated Apr. 12, 2017.

(Continued)

*Primary Examiner* — Timothy C Cleveland
(74) *Attorney, Agent, or Firm* — Jodi A. Reynolds, Esq.; Brian B. Shaw, Esq.; Harter Secrest & Emery LLP

(57) ABSTRACT

A method and apparatus for sterilizing is provided, wherein an item to be sterilized is loaded into a sterilizing cabinet integrated with a sterilizable wheeled case cart, the sterilizing cabinet comprising an interior, the interior being sterilizable; the sterilizable wheeled cart and the affixed sterilizing cabinet is rolled into the floor loading sterilizer; the sterilizable wheeled case cart and the integrated sterilizing cabinet in the floor loading sterilizer is exposed to a sterilizing cycle; and the integrated sterilizable wheeled case cart and sterilizing cabinet are rolled from the floor loading sterilizer, without requiring vertical translation of the sterilizing cabinet relative to the ground or the case cart.

21 Claims, 4 Drawing Sheets

(52) U.S. Cl.
CPC ........... *A61B 2050/105* (2016.02); *A61L 2/28* (2013.01); *A61L 2202/121* (2013.01); *A61L 2202/122* (2013.01); *A61L 2202/14* (2013.01); *A61L 2202/16* (2013.01); *A61L 2202/24* (2013.01)

(58) Field of Classification Search
CPC . A61L 2202/16; A61L 2202/24; A61B 50/13; A61B 50/18; A61B 2050/105
See application file for complete search history.

(56) References Cited

U.S. PATENT DOCUMENTS

| | | | |
|---|---|---|---|
| 9,808,545 B2* | 11/2017 | Mauzerall | ............. A47B 81/00 |
| 2011/0291372 A1 | 12/2011 | Stryker et al. | |
| 2012/0082589 A1 | 4/2012 | Ladison et al. | |
| 2014/0049014 A1 | 2/2014 | Schumacher et al. | |
| 2015/0023839 A1 | 1/2015 | Snyder et al. | |
| 2015/0209456 A1 | 7/2015 | Turbett | |
| 2015/0209462 A1 | 7/2015 | Turbett et al. | |
| 2015/0314026 A1 | 11/2015 | Mauzerall et al. | |

OTHER PUBLICATIONS

European Patent Office, Office Action from corresponding EP Application No. 17744957.6, dated Jun. 30, 2020.
European Patent Office, Extended European Search Report from corresponding EP Application No. 17744957.6, dated Aug. 14, 2019.
Australian Patent Office, Examination Report No. 1 from corresponding AU Application No. 2017212623, dated Nov. 20, 2019.

* cited by examiner

METHOD AND APPARATUS FOR LOADING A FLOOR LOADING STERILIZER

FIELD OF THE INVENTION

Exemplary embodiments of the present disclosure relate to a method and apparatus for presenting items to be sterilized to a sterilization machine, and particularly to a cart and sterilizing cabinet assembly capable of being placed directly into a floor loading (or walk-in) sterilizer, and more particularly to and integrated wheeled case cart and sterilizing cabinet, wherein the case cart and sterilizing cabinet are configured to withstand multiple sterilization cycles.

BACKGROUND OF THE INVENTION

Sterilization is a term referring to any process that eliminates (removes) or kills microbial life, including transmissible agents (such as fungi, bacteria, viruses, or spore forms) present on a surface, contained in a fluid, in medication, or in a compound such as biological culture media. Sterilization can be achieved by applying heat, chemicals, irradiation, high pressure, and filtration or combinations thereof.

In general, surgical instruments and medications that enter an already aseptic part of the body (such as the bloodstream, or penetrating the skin) must be sterilized to a high sterility assurance level. Examples of such instruments include scalpels, hypodermic needles and implantable medical devices (IMD), such as artificial pacemakers. This also includes all of the outer garments worn by the medical personnel, drapes used on or over the patient, and drapes used to divide the sterile portion of an operating room and the non-sterile portion of the operating room.

One method of sterilization involves passing a sterilizing agent, such as steam through a cabinet. For effective sterilization, steam needs to penetrate the cabinet load uniformly. Accordingly, the cabinet must not be overcrowded, and the lids of the bottles and containers must be left ajar. During the initial heating of the chamber, residual air must be removed. Indicators should be placed in the most difficult places for the steam to reach to ensure that steam actually penetrates there.

A filter is typically placed over the vent to keep particles or extraneous materials from entering the cabinet before, during or after the sterilizing process. Once the sterilizing process is completed the filter needs to be removed and inspected by medical professionals to verify the integrity of the sterilizing process was maintained. If it is discovered during the inspection that the filter did not remain intact, the sterilizing process has to be repeated with a new filter.

BRIEF SUMMARY OF THE INVENTION

In view of the foregoing, a method is provided including loading an item to be sterilized into an integrated sterilizing cabinet and sterilizable wheeled case cart, the sterilizing cabinet comprising an interior, the interior being sterilizable; rolling the integrated sterilizable wheeled case cart and sterilizing cabinet into the floor loading sterilizer; exposing the integrated sterilizable wheeled case cart and sterilizing cabinet in the floor loading sterilizer to a sterilizing cycle; and rolling the integrated sterilizable wheeled case cart and sterilizing cabinet from the floor loading sterilizer.

The present disclosure also contemplates an apparatus for presenting items to a floor loading sterilizer, the apparatus comprising: a sterilizable wheeled case cart, the sterilizable wheeled case cart configured to contain one of individually sterilized items or non-sterile items, and comprising a top portion, and a plurality of sterilizable wheels fixedly coupled to a bottom portion of the sterilizable wheeled cart able to freely rotate and support the sterilizable wheeled cart; a sterilizing cabinet, the sterilizing cabinet integrated with the sterilizable wheeled case cart and comprising an interior, the interior configured to contain collectively sterilized items, the interior being sterilizable; and the sterilizable wheeled case cart and the sterilizing cabinet configured to locate the interior at a surgical field compliant height.

The following will describe embodiments of the present disclosure, but it should be appreciated that the present disclosure is not limited to the described embodiments and various modifications of the invention are possible without departing from the basic principle. The scope of the present invention is therefore to be determined solely by the appended claims.

BRIEF DESCRIPTION OF THE SEVERAL VIEWS OF THE DRAWING(S)

FIG. 1 is a perspective view of an operator loading a floor loading sterilizer.

FIG. 2 a front elevational view of a representative floor loading sterilizer.

DETAILED DESCRIPTION OF THE INVENTION

Prior to any surgical procedure, all of the items that will be used during the procedure should be properly sterilized. This includes all of the medical instruments, such as scalpels and needles as well as the outer garments worn by the medical professionals. Typically, each of the fabric items, such as garments and drapes, that are used during a medical procedure are individually sterilized and then wrapped in a sealed bag prior to the medical procedure. This allows the medical professionals to open and unwrap only the items that will be needed for a given procedure while maintaining the sterility of the unused items.

The individually sterilized items are typically kept in a cart, which is more commonly known as a case cart. The purpose of the case cart is twofold. First, the case cart maintains the individually sterilized items in a manner that will sufficiently ensure that the packaging and thus the sterile nature of each of the individually sterilized items is maintained. Second, the case cart provides accessibility and mobility for its contents, which can be wheeled from one area to another with relative ease.

Figure 1:
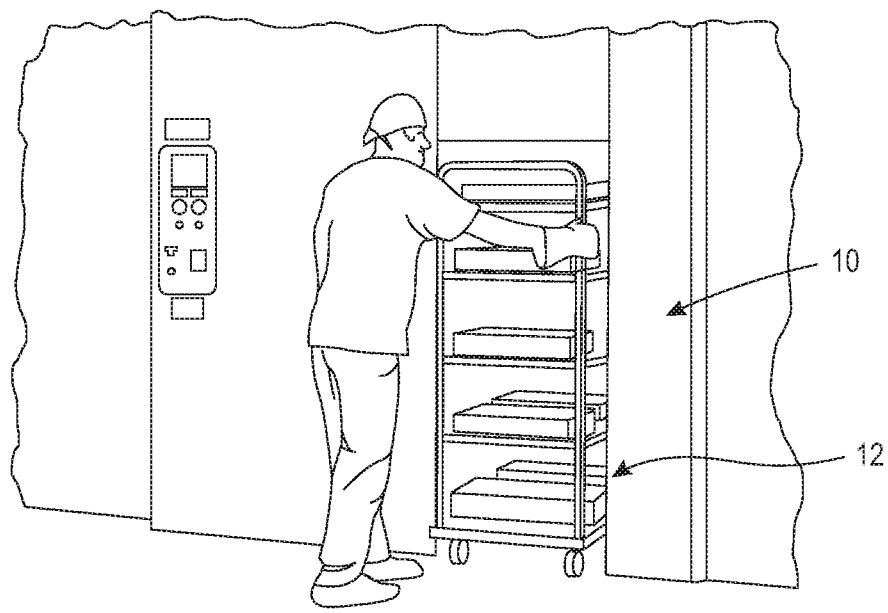
Figure 2:
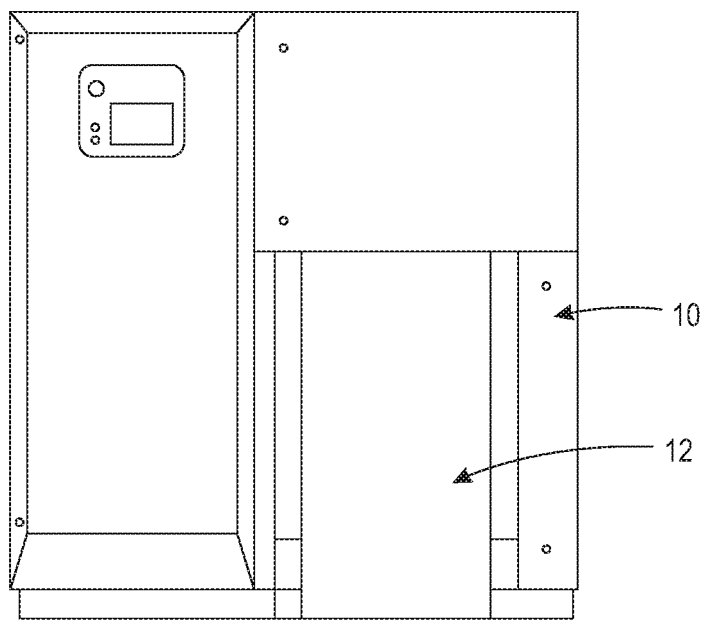

Referring to FIGS. 1 and 2 a representative floor loading (mount) sterilizer 10 as known in the art is shown, wherein the sterilizer includes an access port 12 for receiving a cart. The present system and method are provided for use with commercially available floor loading sterilizers, such as steam sterilizers including Amsco floor loading system from Steris of Mentor, Ohio and floor loading steam sterilizers from Getinge of Rochester, N.Y. and Lake Mary Fla., as well as Belimed of Switzerland. Typical dimensions for the access port 12 range from 20" to 36" wide and 48" to 72" high, wherein the chamber has a depth between approximately 42" to 96". While these are representative dimensions, it is understood the dimensions can vary, wherein the corresponding dimensions of the components of the present system set forth below are correspondingly sized.

Figure 3:
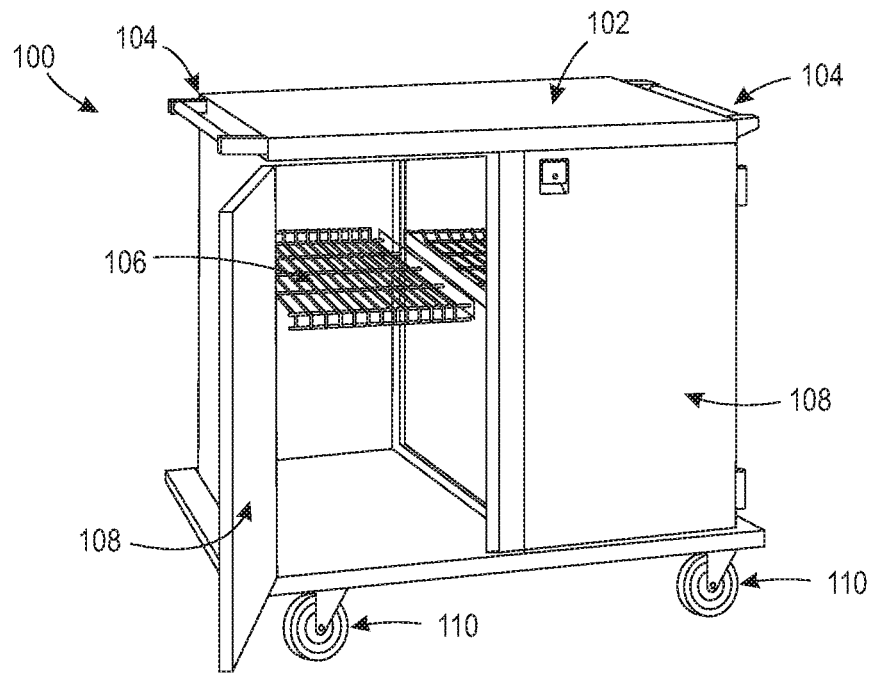
FIG. 3 is a perspective view of a case cart suitable for use in practicing exemplary embodiments of this disclosure.

Shown in FIG. 3 is an exemplary case cart 100. The case cart 100 includes a top 102, push handles 104, shelf 106, doors 108, and wheels 110. The case cart 100 can be constructed out of any durable material that is strong enough to maintain its shape and form under significant weight and also able to be sterilized. Ideally, the case cart 100 is constructed out of a steel or aluminum alloy or a combination thereof, which can withstand multiple cycles through the floor loading sterilizer. It should be understood that case cart 100 is merely an exemplary embodiment of a case cart. Alternative exemplary embodiments of case cart 100 do not include an enclosed interior section, but offers an open midsection with one or multiple shelves.

The top 102 of the case cart 100 provides a surface to integrate a sterilizing cabinet 300. The top 102 is sufficiently rigid to sustain the weight of the sterilizing cabinet (or other like sterilizing device or apparatus). The top 102 may also include a locking mechanism such as clamps, detents, slides, screws, pins as well as welds, bolts or other fasteners which can provide an integral connection between the case cart 100 and the sterilizing cabinet 300. In one configuration, bolts are used to integrate the sterilizing cabinet 300 with the case cart 100. While it is understood the locking mechanism can provide a means to removably affix a sterilizing cabinet to the case cart 100 on the top 102, the locking mechanism can provide an integral or affixed connection between the case cart and the sterilization cabinet. The terms integrated, integration, integrate or integral are used herein to encompass affixable, affixed, coupled, engaged or joined. It is understood the sterilizing cabinet 300 can be integrated with the case cart 100 so as to preclude or permit non-destructive separation of the sterilizing cabinet from case cart.

Further, while described in terms of an integration interface between the top 102 of the case cart 100 and the sterilizing cabinet 300, such description is not meant to limit the configuration of the integration of the case cart and the sterilizing cabinet, as the sterilizing cabinet can be integrated within an interior of the case cart. That is, depending on the specific configuration of the case cart 100, the sterilizing cabinet 300 and the chamber of the floor loading sterilizer 10, the integration interface between the case cart and the sterilizing cabinet can be a shelf or mount within the case cart. In one configuration, the integration interface locates the sterilizing cabinet 300 at the acceptable, proper height for presentation (use) in a surgical field. Pursuant to the Association of periOperative Registered Nurses (AORN), the guideline height for the floor, or bottom, of the sterilizing cabinet 300 for presentation to the surgical or sterile field is waist height. It is contemplated that certain configurations of the integrated system can locate the floor of the sterilizing cabinet 300 at a height between approximately 24 inches to approximately 60 inches.

In further configurations set forth below, the case cart 100, such as the top 102, and the sterilizing cabinet 300 can include mating surfaces or features for integrating the sterilizing cabinet to the case cart.

The push handles 104 of the case cart 100 provide for a user to more easily push and pull the case cart. In the embodiment shown in FIG. 3, push handles 104 are provided on opposite sides of case cart 100. Each of the push handles 104 span from 5% to 100%, or in select configurations more than 100% of the width of the case cart 100. It is understood embodiments of the push handles 104 include the push handles being located on all sides or only on one side of the case cart 100 along with different configurations.

The case cart 100 also includes shelf or shelves 106. FIG. 3 depicts the case cart with only one shelf 106, however, exemplary embodiments of the case cart encompass a plurality of shelves as well as zero shelves. For purposes of the description, the case cart 100 is referred to as incorporating a plurality of shelves. The shelves 106 can be removable or permanently affixed. The shelves 106 are constructed of a material such as stainless steel, aluminum, or alloy that withstand multiple sterilizing cycles within the floor loading sterilizer 10. However, it is understood, the number of or lack of shelves in the case cart 100 is not limiting.

Exemplary embodiments of individually sterilized items include sterile garments, dividers or drapes that are typically used during a procedure or in an operating room. The individually sterilized items are each individually sterilized and then wrapped in a sealed wrapping that maintains the sterility of the item by preventing extraneous materials from coming into direct contact with the individually sterilized items. Non-sterile items include any type of instrument, tool, garment, apparatus, device, or thing that has not been sterilized as well as those that have not been sterilized and can be, will be or is typically used in or in conjunction with a procedure or in an operating room. Non-sterile surgical tape or gauze are non-limiting exemplary embodiments of non-sterile items.

The shelves 106 provide a stable location for maintaining individually sterilized items or non-sterile items. In one exemplary embodiment, the shelves 106 are substantially horizontal and sufficiently rigid to maintain the weight of the sterilizing cabinet 300 or other like sterilizing device or apparatus. Shelf or shelves 106 may also include a locking mechanism as a means to affix, removably or integrally, the shelves 106 within the case cart 100, as well as integrating the sterilizing cabinet 300 and the case cart.

The case cart 100 can include the door or doors 108. For purposes of the description, the case cart 100 is referred to as incorporating a plurality of doors. However, it is understood, the number of or lack of doors in the case cart is not limiting. That is, the case cart 100 can be free of doors, wherein there are no doors connected to the case cart. In configurations having doors, the doors 108 are able to open and close for access to the interior of case cart 100, which is typically in the midsection of case cart 100. The doors 108 are physically connected to case cart 100. The doors 108 can be attached through the use of a hinge or hinges which allows the doors to swing open. The doors 108 can also include a latch or lock for securely keeping the doors 108 from opening when not desired. It should be appreciated that exemplary embodiments of door or doors 108 include any mechanism that allows for the doors 108 to move from an open position to a closed position to provide access to the interior of case cart 100.

In one configuration, the doors 108 pivot about corresponding corners of the case cart 100, such that in the open configuration, the doors are at least substantially parallel to an adjacent portion or side of the case cart. For example, the doors 108 opening to provide access from the side of the case cart, the doors sufficiently rotate about the hinge axis to lie parallel to end walls of the case cart.

As set forth herein, exemplary embodiments of the case cart 100 provide that the interior of the case cart is of the shape and size such that an entire sterilizing cabinet 300 can reside within the interior of the case cart and the doors 108 are free to open and close without being obstructed should a sterilizing cabinet reside within the interior of the case cart.

FIG. 3 also discloses casters or wheels 110 on the case cart 100. The wheels 110 provide for the case cart 100 to be moved from one location to another. The wheels 110 are configured to hold a significant amount of weight and are still able to freely rotate such that when a user pushes or pulls case cart 100, the wheels 110 rotate in a direction of the user's actions. Embodiments of the wheels 110 include the ability for the wheels to be selectively placed into a locked position wherein at least rotation of the wheels 110 is prohibited. It is contemplated an embodiment can place the wheels 110 in a locked position which precludes rotation of the wheels about a translation axis that is parallel to the ground and an orientation axis that is perpendicular to the ground. Exemplary embodiments of case cart 100 include the four wheels 110 located at each corner of the bottom of case cart 100. However, it should be appreciated that alternative embodiments of case cart 100 include more or less than four wheels as well as different arrangements.

The wheels 110, as well as any interconnected mechanism to the case cart 100, are sterilizable. That is, the wheels 110 can be repeatedly sterilized to provide a repeatability of the sterilization as well as sustainability of operation of the wheels. Representative wheels 110 include those identified as high temperature casters as sold by Service Caster Corporation of West Reading, Pa.

Figure 4:
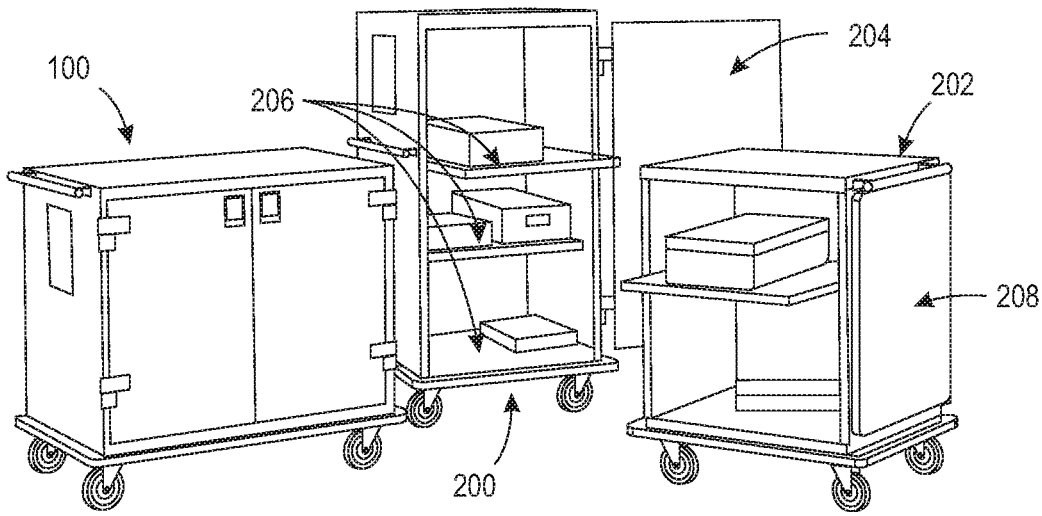
FIG. 4 depicts numerous case carts suitable for use in practicing exemplary embodiments of this disclosure.

Exemplary embodiments of case cart 100 include numerous shapes and sizes. FIG. 4 depicts three such case carts. Shown in FIG. 4 is case cart 100, case cart 200, and case cart 202. As illustrated in FIG. 4, case cart 200 has almost all of the characteristics of case cart 100 except that it is taller and includes a single door 204 and multiple shelves 206. Case cart 202 also has almost all of the characteristics of case cart 100 except that it too only includes a single door 208. It should be appreciated that case cart 100, the case cart 200, and the case cart 202 though they may appear differently, each of their elements (i.e., the doors, the wheels, the shelves, and the top) are configured to functionally perform the similar task of providing mobility and the ability to maintain individually sterilized items and are sized to be operably received within the floor loading sterilizer 10 without lifting or vertical translation.

However, each case cart is sized to be operably received within the floor loading sterilizers. As set forth below, depending on the configuration of the case cart 100, the sterilizing cabinet 300 and the floor loading sterilizer, the case cart and the sterilizing cabinet are sized to be operably received within the floor loading sterilization system by rolling the integrated case cart and sterilizing cabinet directly into the floor loading sterilizer.

Figure 5:
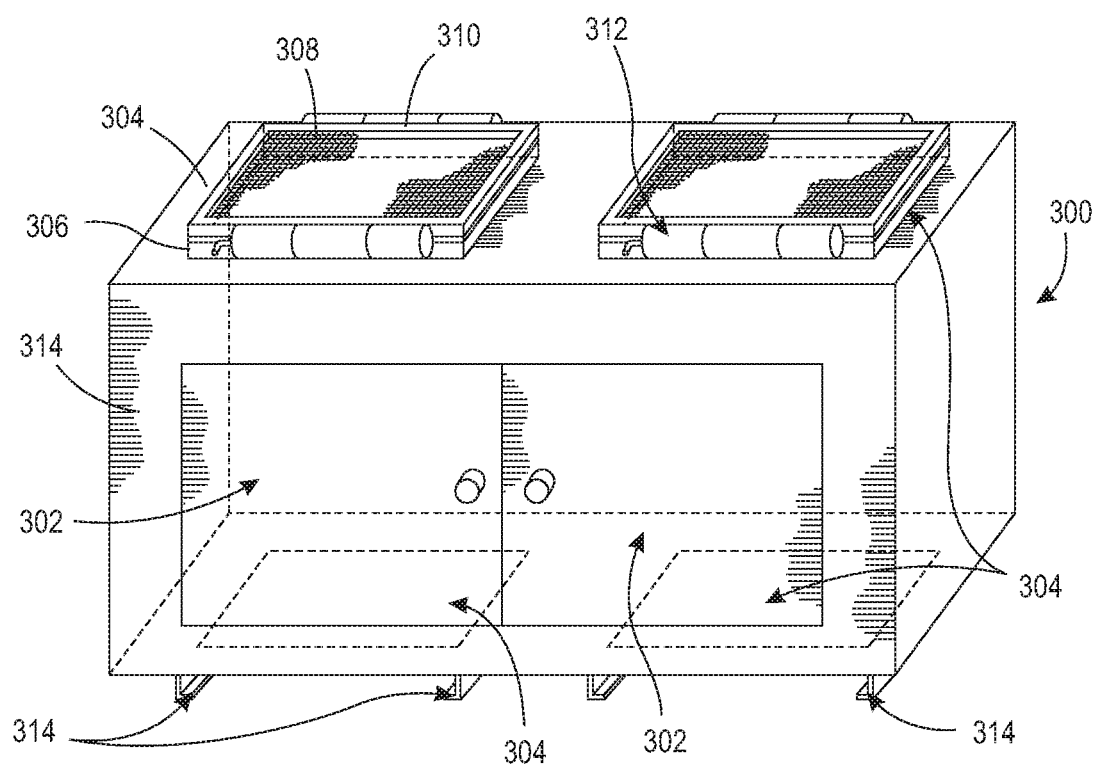
FIG. 5 is a perspective view of a sterilizing cabinet suitable for use in practicing exemplary embodiments of this disclosure.

FIG. 5 depicts a perspective view of a cabinet or sterilizing cabinet 300. Exemplary embodiments of sterilizing cabinet 300 are able to collectively sterilize items that are placed within its interior. Exemplary embodiments of the sterilizing cabinet 300 include any type of cabinet with the ability to be repeatedly subjected to a sterilizing process. The sterilizing cabinet 300 can further include the ability to use a filter or filters for passing a sterilizing agent into and out of the sterilizing cabinet. Shown in FIG. 5 is sterilizing cabinet 300 with a door or doors 302, vents 304, primary filters 306, secondary filters 308, filter holders 310, and filter lock 312.

While set forth in terms of a plurality of doors 302, it is understood the sterilizing cabinet 300 can incorporate only a single door or even no door. The doors 302 are able to open and close for access to the interior of sterilizing cabinet 300. The doors 302 are physically connected to sterilizing cabinet frame 314. The doors 302 can be attached through the use of a hinge or hinges which allows the doors to swing open. Alternatively, the doors 302 can be removable from sterilizing cabinet 300 through the use of clamps (not shown). It should be appreciated that exemplary embodiments of the doors 302 include any mechanism that allows for the doors 302 to move from an open position to a closed position to provide access to the interior of sterilizing cabinet 300.

The sterilizing cabinet 300 in the embodiment illustrated in FIG. 5 includes four vents 304. Embodiments of the sterilizing cabinet 300 provide that the sterilizing cabinet 300 may include one or more vents 304. As depicted in FIG. 5, the sterilizing cabinet 300 includes two vents 304 on the top of sterilizing cabinet and two vents 304 on the bottom of sterilizing cabinet. The vents 304 provide numerous openings for the passage of a sterilizing agent, such as sterilizing steam. The openings in vents 304 can be relatively small holes or slits. In an alternative embodiment, the vents 304 are fenestrated.

A primary filter 306 in conjunction with a filter holder 310 covers the vent 304. The primary filter 306 with the filter holder 310 forms a sealed interface with the adjacent portions of the sterilizing cabinet 300 such that during the operation of a sterilizing cycle, any sterilizing steam that passes through the vents 304 must also pass through the primary filter 306. Embodiments of primary filter 306 provide that primary filter 306 can be made of any porous material that (1) allows for the passage of sterilizing steam through sterilizing cabinet 300 and (2) prevents extraneous materials from passing through primary filter 306 and entering vent 304. Primary filter 306 is removable from sterilizing cabinet 300 and is typically replaced with a new filter following each sterilizing cycle.

Secondary filter 308 resides on top of primary filter 306 in filter holder 310. Secondary filter 308 covers primary filter 306 and forms a sealed interface with primary filter 306 in conjunction with filter holder 310 such that any sterilizing agent, such as sterilizing steam that passes through vent 304 must then pass through primary filter 306 and secondary filter 308. Secondary filter 308 can be made of any type of porous material that (1) allows for the passage of sterilizing steam from sterilizing cabinet 300 and primary filter 306 and (2) prevents extraneous materials from passing through secondary filter 308.

Exemplary embodiments of sterilizing cabinet 300 also include configurations wherein sterilizing cabinet 300 only includes a primary filter 306 and does not include the use of a secondary filter 308. Exemplary embodiments of this disclosure also provide for the embodiment that employs the use of a secondary filter 308 to form a sealed periphery with primary filter 306. In another exemplary embodiment the sealed interface between the primary filter 306 and the adjacent portion of either the sterilizing cabinet 300 is independent of an interface between secondary filter 308 and primary filter 306. In one exemplary embodiment, the primary filter 306 and the secondary filter 308 are coextensive. In another exemplary embodiment, primary filter 306 and secondary filter 308 have different filter properties. For instance, primary filter 306 and secondary filter 308 may filter different elements of the sterilizing agent, which exits sterilizing cabinet 300 during a sterilization cycle. In an alternative exemplary embodiment, primary filter 306 and secondary filter 308 have similar filter properties. Another exemplary embodiment provides that primary filter 306 and secondary filter 308 are different colors.

It is contemplated that in the no door configuration of the sterilizing cabinet 300, one of the primary filter 306, filter holder 310 and/or secondary filter 308 or a combination can be used to effectively close the sterilizing cabinet.

As the sterilizing cabinet 300 and the case cart 100 can be integrated, it is contemplated each can include cooperating, mating or engaging features that provide for the integral connection of the sterilizing cabinet and the case cart. While the present description sets forth certain components of the engaging features on the sterilizing cabinet 300 and complementary features on the case cart 100, it is understood the location of the engaging features can be switched between the sterilizing cabinet and the case cart.

In one configuration, sterilizing cabinet 300 includes legs 314, which reside on the bottom of sterilizing cabinet 300. Legs 314 provide spacing between the case cart 100 and the bottom primary filter 306, secondary filter 308 and filter holder 310 upon integration of the sterilizing cabinet and the case cart. In an alternative embodiment, legs 314 provide spacing between the case cart 100 and the bottom primary filter 306 and filter holder 310. In this alternative embodiment, sterilizing cabinet 300 does not contain secondary filter 308. It should be appreciated that legs 314 as depicted in FIG. 5 are only exemplary embodiments of the possible configuration of legs 314.

For example, in one embodiment, the legs 314 include a locking or attachment mechanism that provides a means for integrated sterilizing cabinet 300 to the case cart 100 to an integral configuration. As set forth above, the case cart 100 and the sterilizing cabinet 300 are configured to be integrated by any of a variety of mechanisms, wherein the case cart and the sterilizing cabinet are effectively affixed for purposes of locating the case cart and the sterilizing cabinet in the floor loading sterilizer, operation of the floor loading sterilizer upon the integrated sterilizing cabinet and case cart, removal of the integrated sterilizing cabinet and case cart from the floor loading sterilizer and delivery or transport of the integrated sterilizing cabinet and case cart to present to the surgical field, wherein the sterilizing cabinet is within an acceptable height range of the surgical field between approximately 24 inches and approximately 60 inches.

Integrating the sterilizing cabinet 300 to the case cart 100 includes the recited affixing, locking, attaching, coupling and engaging, as well as integral construction in which common material is used between the case cart and the sterilizing cabinet. It is contemplated the integration substantially precludes altering the height of the sterilizing cabinet 300 relative to the case cart 100.

However, it is understood an adjustment mechanism can be included between the case cart 100 and the sterilizing cabinet 300 to allow for adjustments, such as leveling. Such adjustment mechanism provides for such height alterations within the integrated case cart 100 and sterilizing cabinet 300 to address tolerances or leveling issues. The adjustment mechanism can include, but is not limited to threaded couplings, cams and shims. It is anticipated the throw or range of the adjustment mechanism is less than 50%, and likely less than 10% of the acceptable height range of the surgical field between approximately 24 inches and approximately 60 inches.

With respect to the sterilizing cabinet 300 shown in FIG. 5, filter holder 310 is provided for maintaining primary filter 306 and secondary filter 308. In embodiment, filter holder 310 only maintains primary filter 306. Exemplary embodiments of filter holder 310 include a hinge which allows portions of filter holder 310 to swing open about the hinge such that primary filter 306 and secondary filter 308 can be removed or placed independent of one another. In other words, filter holder 310 allows for secondary filter 308 to be released and removed from filter holder 310 while simultaneously maintaining primary filter's 306 seal with sterilizing cabinet 300 over vent 304.

Figure 6:
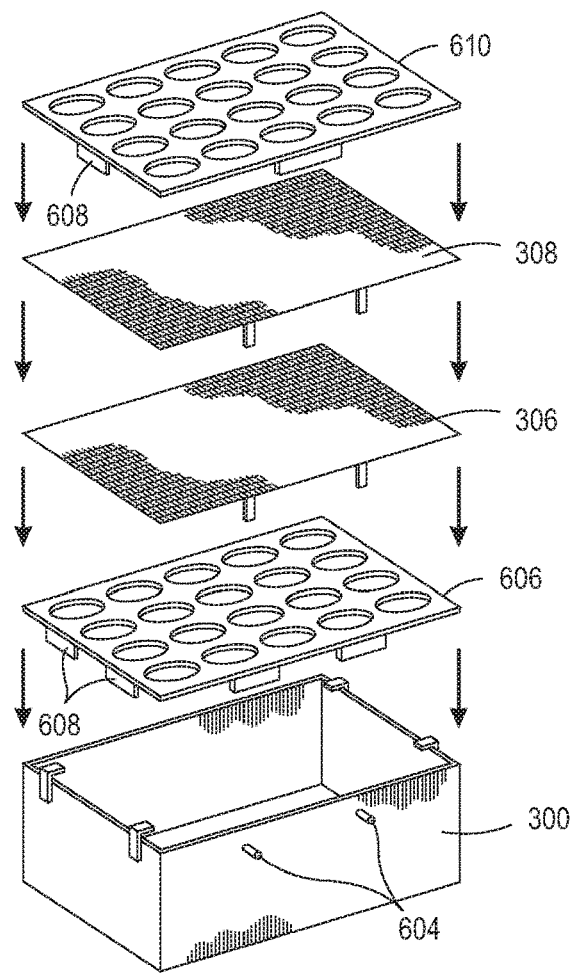
FIG. 6 is a perspective view of a filter arrangement suitable for use in practicing exemplary embodiments of this disclosure.

FIG. 6 is a perspective view of the construction of an alternative arrangement of sterilizing cabinet 300. As shown in FIG. 6, filter door 606 with clamps 608 attach around the frame of sterilizing cabinet 300. Primary filter 306 is placed on top of filter door 606 and attaches to sterilizing cabinet 300 at hooks 604. Secondary filter 308 is placed on top of primary filter 306 and also attaches to sterilizing cabinet 300 at hooks 604. Filter door 610 is then placed on top of secondary filter 308 and attached to sterilizing cabinet 300 with clamps 608. Exemplary embodiments of filter doors 606 and 608 include numerous holes or openings along their surface, which allow for the passage of sterilizing steam. In an alternative exemplary embodiment, secondary filter 308 is removed and only primary filter 306 is placed between filter doors 606 and 608.

Figure 7:
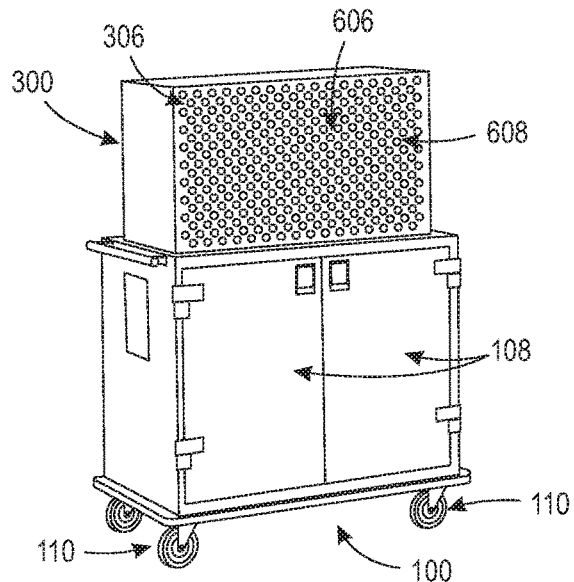
FIG. 7 is a perspective view of a device suitable for use in practicing exemplary embodiments of this disclosure.

FIG. 7 illustrates an assembled or affixed case cart 100 and sterilizing cabinet 300, wherein the case cart and the sterilizing cabinet are integrated. While the sterilizing cabinet 300 is located on top of the case cart 100, it is understood as set forth above the sterilizing cabinet can be located within the case cart, wherein the sterilizing cabinet remains within the required surgical field height throughout entire loading, sterilizing, unloading and presenting process. That is, vertical lifting of an unloaded or loaded sterilizing cabinet relative to the case cart 100 is precluded.

As shown in FIG. 7, before, during and after a sterilizing cycle in the floor loading sterilizer, the sterilizing cabinet 300 is integrated with the case cart 100. Following the sterilizing cycle, the sterilizing cabinet 300 remains integrated with case cart 100 as shown in FIG. 7 for presentation to the surgical field. Since sterilizing cabinet 300 may be quite heavy, depending on the contents of sterilizing cabinet 300, the use of a lift or mechanical lift is avoided as the sterilizing cabinet is integrated with the case cart 100.

As shown in FIG. 7, the sterilizing cabinet 300, which includes filter doors 606 and 608, primary filter 306 is integrated with the case cart 100. It should be appreciated that sterilizing cabinet 300 and case cart 100 although not explicitly depicted in FIG. 7 may include any of the elements previously described in this disclosure as it relates to sterilizing cabinet 300 and case cart 100.

In other exemplary embodiments, the integrated case cart 100 and sterilizing cabinet 300 may include a processor, a memory including computer program instructions, a display, a controller, and a transmitter/receiver for tracking the contents of the integrated system. In this embodiment, the memory or non-transitory computer-readable memory including computer program instructions which when executed on the processor of integrated system can track when each item enters or exits sterilizing cabinet 300 and case cart 100. This tracking system can be performed any type of unit tracking system, such as through the use of barcode scanners or RFID tags as known in the respective art. The display will provide communication and display on demand, the list of items within sterilizing cabinet 300 and case cart 100 and when a particular item was removed. Additionally, a transmitter/receiver can communicate via wired or wireless networks the same inventory information shown on the display. The controller will allow a user to access the inventory of integrated case cart 100 and sterilizing cabinet 300.

Thus, the present system provides for loading one of an individually sterilized item or a non-sterile item into at least one of an integrated wheeled sterilizable case cart 100, the case cart comprising a plurality of wheels fixedly coupled to a bottom portion of the case cart able to freely rotate and support the cart and sterilizing cabinet 300; loading the integrated case cart and sterilizing cabinet into the floor loading sterilizer; performing at least one cycle of the floor loading sterilizer; removing the integrated case cart and sterilizing cabinet from the floor loading sterilizer, transporting the integrated case cart and sterilizing cabinet and presenting the integrated case cart and sterilizing cabinet to a surgical field, wherein sterilizing cabinet remains within the acceptable height range of the surgical field during each of the loading, sterilizing, removing, transporting and presenting steps.

In an alternative configuration, the present methods include loading an item to be sterilized into an integrated sterilizing cabinet and sterilizable wheeled case cart, rolling the integrated sterilizable wheeled case cart and sterilizing cabinet into the floor loading sterilizer; exposing the integrated sterilizable wheeled case cart and sterilizing cabinet in the floor loading sterilizer to a sterilizing cycle; rolling the integrated sterilizable wheeled case cart and sterilizing cabinet from the floor loading sterilizer, wherein the integrated sterilizing cabinet and sterilizable wheeled case cart present items in the sterilizing cabinet at the acceptable height to the surgical field.

Thus, the present disclosure provides a method and apparatus for loading individually sterilized items into an integrated case cart and sterilizing cabinet, and rolling the integrated system into a floor loading sterilizer; cycling the floor loading sterilizer and rolling the integrated case cart and sterilizing cabinet from the floor loading sterilizer and rolling the integrated system for presentation to a surgical field, wherein each step is free from vertical translation of the sterilization cabinet.

It will be appreciated that variants of the above-disclosed and other features and functions, or alternatives thereof, may be combined into many other different systems or applications. Various presently unforeseen or unanticipated alternatives, modifications, variations, or improvements therein may be subsequently made by those skilled in the art, which are also intended to be encompassed by the following claims.

The invention claimed is:

1. An apparatus for presenting items to a floor loading sterilizer, the apparatus comprising:
   (a) a sterilizable wheeled case cart, the sterilizable wheeled case cart configured to contain one of individually sterilized items or non-sterile items, and comprising a top portion, and a plurality of sterilizable wheels fixedly coupled to a bottom portion of the sterilizable wheeled case cart able to freely rotate and support the sterilizable wheeled case cart;
   (b) a sterilizing cabinet, having an interior, an access port, a vent-free bottom, and a door moveable between an open position permitting passage through the access port to the interior of the sterilizing cabinet and a closed position precluding passage through the access port, at least one of the sterilizing cabinet and the door having a vent port and at least one filter overlying the vent port, the sterilizing cabinet in integrated form with the sterilizable wheeled case cart wherein the sterilizing cabinet and sterilizable wheeled case cart cannot be separated, the interior of the sterilizing cabinet sterilizable and configured to contain collectively sterilized items; and
   (c) the sterilizable wheeled case cart and the sterilizing cabinet configured to be received within a floor loading sterilizer and locate the interior at a surgical field compliant height.

2. The apparatus according to claim 1, wherein the sterilizable wheeled case cart is configured to contain both individually sterilized items and non-sterile items.

3. The apparatus according to claim 1, the apparatus wherein the interior of the sterilizing cabinet is adjustable within a range in the surgical field compliant height.

4. The apparatus according to claim 1, wherein the sterilizing cabinet comprises at least two filters overlying the vent port and forming a sealed interface with an adjacent portion of the one of the sterilizing cabinet and the door.

5. The apparatus according to claim 1, wherein the sterilizable wheeled case cart comprises at least one door, the at least one door connected to the sterilizable wheeled case cart, the at least one door moveable between an open position permitting passage through an access port to an interior of the sterilizable wheeled case cart having a plurality of shelves, and a closed position precluding passage through the access port.

6. The apparatus according to claim 1, wherein the sterilizable wheeled case cart is free of a door.

7. The apparatus according to claim 1, wherein the door of the sterilizing cabinet comprises the vent port.

8. The apparatus according to claim 1, wherein the integrated sterilizable wheeled case cart and sterilizing cabinet is precluded from a height adjustment of the sterilizing cabinet relative to the sterilizable wheel case cart.

9. The apparatus according to claim 8, wherein the sterilizing cabinet further comprises at least one filter overlying the vent port on the door and forming a sealed interface with an adjacent portion of one of the sterilizing cabinet and the door.

10. A method of presenting items to a floor loading sterilizer using the apparatus of claim 1, the method comprising:
    (a) loading an item to be sterilized into the interior of the sterilizing cabinet; and
    (b) rolling the integrated sterilizable wheeled case cart and sterilizing cabinet into the floor loading sterilizer; and
    (c) exposing the integrated sterilizable wheeled case cart and sterilizing cabinet in the floor loading sterilizer to a sterilizing cycle.

11. The method of claim 10, further comprising, prior to rolling the integrated sterilizable wheeled case cart and sterilizing cabinet into the floor loading sterilizer, disposing at least one separately wrapped item to be sterilized onto the sterilizable wheeled case cart.

12. The method of claim 10, wherein the sterilizable wheeled case cart comprises at least one door, the at least one door connected to the sterilizable wheeled cart, the at least one door moveable between an open position permitting passage through an access port to an interior of the sterilizable wheeled cart and a closed position precluding passage through the access port, a plurality of shelves being located in the interior of the sterilizable wheeled case cart.

13. The method of claim 10, wherein the sterilizing cabinet further comprises at least one filter overlying the vent port and forming a sealed interface with an adjacent portion of one of the sterilizing cabinet and the door.

14. The method of claim 13, wherein the sterilizing cabinet comprises at least two filters overlying the vent port and forming a sealed interface with an adjacent portion of the one of the sterilizing cabinet and the door.

15. The method of claim 14, wherein the sterilizable wheeled case cart and the sterilizing cabinet comprise a height adjustment, the height adjustment adapted to adjust a height of the sterilizing cabinet relative to the wheels, the height adjustment being limited to within a surgical field compliant range.

16. The method of claim 10, wherein the sterilizable wheeled case cart and the sterilizing cabinet are rolled into the floor loading sterilizer without a height adjustment of the sterilizing cabinet relative to the sterilizable wheeled case cart.

17. The method of claim 10, the method further comprising rolling the integrated sterilizable wheeled case cart and sterilizing cabinet from the floor loading sterilizer and rolling the integrated sterilizable wheeled case cart and sterilizing cabinet to a surgical field.

18. The method of claim 10, wherein rolling the integrated sterilizable wheeled case cart and sterilizing cabinet into the floor loading sterilizer is independent of a height adjustment of the sterilizing cabinet relative to the sterilizable wheeled case cart.

19. The method of claim 10, wherein each of the loading, rolling and exposing steps is independent of vertical translation of the sterilizing cabinet relative to the floor.

20. The method of claim 10, wherein each of the loading, rolling and exposing steps is independent of vertical translation of the sterilizing cabinet relative to the case cart.

21. The method of claim 10, wherein the sterilizable wheeled case cart is free of a door.

* * * * *